United States Patent [19]
Van Tilburg

[11] Patent Number: 4,589,876
[45] Date of Patent: May 20, 1986

[54] SANITARY NAPKIN

[75] Inventor: Kees J. Van Tilburg, Cincinnati, Ohio

[73] Assignee: The Procter & Gamble Company, Cincinnati, Ohio

[21] Appl. No.: 591,621

[22] Filed: Mar. 20, 1984

Related U.S. Application Data

[63] Continuation-in-part of Ser. No. 511,118, Jul. 5, 1983.

[51] Int. Cl.$^4$ .............................................. A61F 13/16
[52] U.S. Cl. .................................. 604/385 R; 604/393
[58] Field of Search ................ 604/381, 387, 375, 370, 604/395

[56] References Cited

U.S. PATENT DOCUMENTS

| | | | |
|---|---|---|---|
| 2,787,271 | 4/1957 | Clark | 604/375 |
| 3,397,697 | 8/1968 | Rickard | 604/370 |
| 4,285,343 | 8/1981 | McNair | 604/387 |

*Primary Examiner*—C. Fred Rosenbaum
*Assistant Examiner*—Karen L. Kaechele
*Attorney, Agent, or Firm*—Thomas J. Slone; Fredrick H. Braun; Richard C. Witte

[57] ABSTRACT

A sanitary napkin. The sanitary napkin comprises a central absorbent pad and flaps extending from each longitudinal edge of the central absorbent pad. The body of each flap contains a flexible axis about which the flap can fold on itself. The sanitary napkin preferentially bends at the line of juncture between each flap and the longitudinal edge of the central absorbent pad. When the sanitary napkin is in a panty for use, each flap bends upwardly at the lines of juncture between the flaps and the longitudinal edges of the central absorbent pad to form the base of a wall. This wall extends to the flexible axis in the body of the flap which is folded around the edge of the crotch portion of the panty. The sanitary napkin of the present invention provides effective protection to the user during the menstrual period by preventing body and clothing soiling while being comfortable to wear.

15 Claims, 11 Drawing Figures

SANITARY NAPKIN

CROSS-REFERENCE TO RELATED APPLICATION

This is a continuation-in-part of U.S. patent application Ser. No. 511,118 filed July 5, 1983.

BACKGROUND INFORMATION

This invention relates to a sanitary napkin. More particularly, this invention relates to a sanitary napkin that comprises a central absorbent pad that contains a flap extending from each longitudinal edge of the central absorbent pad. The body of each flap contains a flexible axis about which the flap can fold on itself. The sanitary napkin preferentially bends at the line of juncture of each flap and the longitudinal edge of the central absorbent pad. When the sanitary napkin is in a panty for use, each flap bends upwardly at the line of juncture of the flap and longitudinal edge of the central absorbent pad to form the base of a wall. The wall extends to the flexible axis in the body of the flap which is folded around the edge of the crotch portion of the panty. The sanitary napkin of the present invention provides extremely effective protection to the user during the menstrual period by preventing panty, body and clothing soiling while at the same time providing the utmost in comfort.

Clark, in U.S. Pat. No. 2,787,271 issued on Apr. 2, 1957, describes a sanitary napkin comprising a rectangular central pad and a pair of lateral flaps fabricated integrally with the pad. These flaps are adapted to fold downwardly and bear against the opposed inner surfaces of the thighs of the wearer to arrest any overflow from the central pad which would normally stain clothing. This sanitary napkin is so fabricated that the lateral flaps will bend downwardly along straight parallel hinge lines defining the respective sides of the central pad. The central pad has a core body which is a soft, absorbent, fibrous material, such as absorbent cotton, and which extends without interruption into the lateral flaps. The hinges are formed by compressing (as by steam pressing with relatively sharp-edged pressing tools) along the lateral margins of the core body in the central pad.

Rickard, in U.S. Pat. No. 3,397,697 issued Aug. 20, 1968, describes a disposable sanitary shield for undergarments. This device comprises an elongate sheet of flexible material divided into at least two panels which are joined by an intermediate neck-like portion. The edge portions of one of the panels adjacent the neck-like portion comprises opposed wing-like flaps adapted to be folded over each other and to confine and encircle the crotch portion of a panty undergarment. The width of the crotch portion of the panty is thus restricted by an encircling absorbent band which is in freely slideable relationship with the crotch portion of the panty.

McNair, in U.S. Pat. No. 4,285,343 issued Aug. 25, 1981, describes a sanitary napkin comprising a central elongate absorbent pad element having side panels extending laterally therefrom. The side panels may be formed either intregally with the central element or they may be formed separately and secured to the longitudinal edges of the central absorbent pad. Lines of common juncture between the central element and the side panels must be flexible so that each side panel can be folded about the respective lateral edge of the central absorbent pad and toward the backside of the central element when the device is used. In use, the central element is adhesively secured to the innerside of the crotch portion of the undergarment and each side panel is folded over to encompass at least half of the outer surface of the crotch portion of the undergarment.

SUMMARY OF THE INVENTION

The present invention relates to a sanitary napkin that includes a central absorbent pad that comprises a liquid pervious topsheet, a liquid impervious backsheet and an absorbent core interposed between the topsheet and backsheet. Each longitudinal edge of the central absorbent pad has a flap extending from it. The sanitary napkin preferentially bends at the line of juncture of each flap and the longitudinal edge of the central absorbent pad. Each flap preferably comprises a liquid pervious topsheet, a liquid impervious backsheet and an absorbent core interposed between the topsheet and backsheet. Additionally, each flap has a flexible axis located in the body of the flap which allows the flap to be folded on itself. In a preferred embodiment, each entire flap is flexible.

The sanitary napkin of the present invention provides numerous benefits. When the sanitary napkin is in use, a gasket-like seal is formed between the body of the user and the flaps along the flexible axis in the body of the flaps. This seal assists in preventing the menstrual fluid from penetrating beyond the flexible axes in the body of the flaps. Additional benefits result from the sanitary napkin preferentially bending at the line of juncture of each flap and the longitudinal edge of the central absorbent pad. Inherent bunching, defined below, causes the formation of flow channels, also defined below, being formed essentially only in the central absorbent pad, i.e. not the flaps. Also, the sanitary napkin can withstand much forced bunching, defined below, before flow channels are formed. Further, even if the forced bunching is harsh enough to create flow channels, the channels will be limited to the central absorbent pad and, therefore, the gasket-seal will remain intact and, thus, assist in preventing the menstrual fluid from penetrating beyond the flexible axes in the body of the flaps. Finally, even if the forced bunching is so great that flow channels are created in both the central absorbent pad and the flaps, the menstrual fluid is restrained from penetrating beyond the flexible axes in the body of the flaps.

DESCRIPTION OF THE PREFERRED EMBODIMENTS

Figure 1:
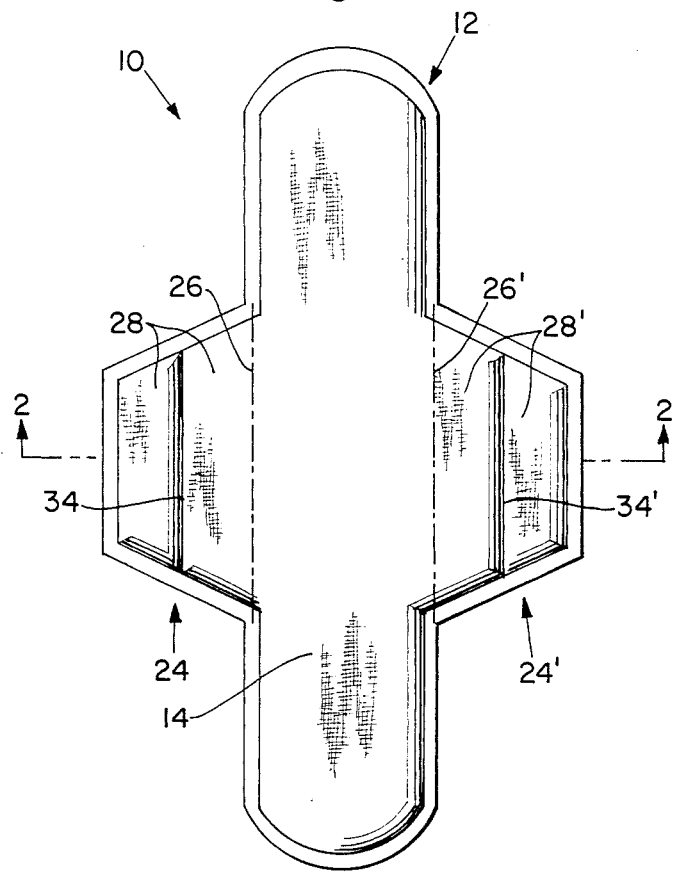
FIG. 1 is a plan view of a preferred sanitary napkin of the present invention.
Figure 2:
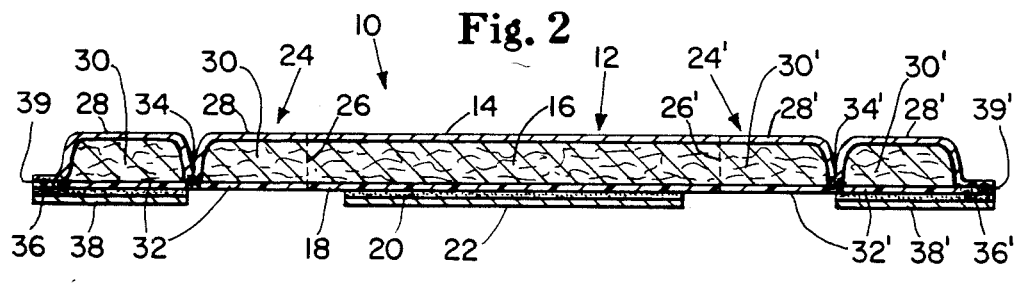
FIG. 2 is a sectional view taken along line 2—2 of FIG. 1.

A preferred embodiment of the sanitary napkin of the present invention is shown in FIGS. 1 and 2. The sanitary napkin is generally referred to by reference numeral 10. Sanitary napkin 10 comprises a central absorbent pad which is generally referred to by reference numeral 12. Central absorbent pad 12 is comprised of liquid pervious topsheet 14, absorbent core 16 and liquid impervious backsheet 18. Secured to backsheet 18 is a layer of adhesive 20 which is covered by removable release liner 22. Extending from each longitudinal edge of the central absorbent pad 12 are flaps 24 and 24'. Flaps 24 and 24' are preferably of similar configuration and, therefore, the detailed description of flap 24 will be understood to be applicable to the 24'. A line of juncture 26 is formed where flap 24 joins the longitudinal edge of central absorbent pad 12. Flap 24 comprises liquid pervious flap topsheet 28, flap absorbent core 30 and liquid impervious flap backsheet 32. Flap 24 is flexible along an axis 34. Secured along the outer edge of flap backsheet 32 is a layer of flap adhesive 36 which is covered by removable flap release liner 38.

Topsheet 14 is liquid permeable and, when sanitary napkin 10 is in use, is in close proximity to the skin of the user. Topsheet 14 is compliant, soft feeling and non-irritating to the user's skin. It can be made from any of the conventional materials for this type of use. Nonlimiting examples of suitable materials that can be utilized as the topsheet 14 are woven and nonwoven polyester, polypropylene, nylon, and rayon are formed thermoplastic films, with formed films being preferred. Suitable formed films are described in U.S. Pat. No. 4,324,246 issued to Mullane and Smith on Apr. 13, 1982 and U.S. Pat. No. 4,342,314 issued to Radel and Thompson on Aug. 3, 1982, both of which patents are incorporated herein by reference. The formed films are preferred for topsheet 14 because they are pervious to liquids and yet non-absorbent. Thus, the surface of the formed film, which is in contact with the body, remains dry and is more comfortable to the wearer.

In preferred embodiments of the present invention, the outer surface of topsheet 14 is treated with a surfactant. Treating the outer surface of topsheet 14 with surfactant renders such surface more hydrophilic which results in liquid penetrating topsheet 14 faster than if the surface were not treated. This diminishes the likelihood that the menstrual fluid will flow off topsheet 14, which results in clotting and body soiling, rather than being absorbed by absorbent core 16. It is preferred that the surfactant be substantially evenly and completely distributed throughout the outer surface of topsheet 14. This can be accomplished by any of the common techniques well known to those skilled in the art. For example, the surfactant can be applied to topsheet 14 by spraying, by padding or by the use of transfer rolls.

In preferred embodiments, the inner surface of topsheet 14 is secured in contacting relation to absorbent core 16. This contacting relationship results in liquid penetrating the topsheet 14 faster than if it were not in contact with absorbent core 16. Topsheet 14 can be maintained in contact with the absorbent core 16 by applying adhesive, preferably in spaced limited areas, to the inner surface of the topsheet 14. Examples of suitable adhesives used for such purpose include the acrylic emulsion E-1833BT manufactured by the Rohm & Haas Company, Philadelphia, Pa. and the acrylic emulsion WB 3805 manufactured by H. B. Fuller Company of St. Paul, Minn. The adhesives can be applied by the same methods as the surfactant is applied to the outer surface of topsheet 14.

Referring again to FIGS. 1 and 2, it can be seen that absorbent core 16 is positioned between topsheet 14 and backsheet 18. Absorbent core 16 provides the absorptive means for absorbing the menstrual fluid. Absorbent core 16 is generally compressible, conformable and non-irritating to the user's skin. It can comprise any material used in the art for such purpose. For example, suitable materials are layers of tissue paper or fibrated comminution pulp, (known as airfelt), with fibrated comminution pulp being preferred.

Backsheet 18 is impervious to liquids and, thus, prevents menstrual fluid which may be expressed from absorbent core 16 from soiling the body or clothing of the user. Any backsheet material used in the art for such purpose can be utilized herein. Suitable materials are embossed or nonembossed polyethylene films and laminated tissue.

The outer surface of backsheet 18 is coated with adhesive 20. Adhesive 20 provides a means for securing central absorbent pad 12 in the crotch portion of a panty. Any adhesive or glue used in the art for such purpose can be used herein, with pressure sensitive adhesives being preferred. Suitable adhesives are Century A-305-IV manufactured by the Century Adhesives Corporation and Instant Lok 34-2823 manufactured by the National Starch Company. Also, before sanitary napkin 10 is placed in use, the pressure sensitive adhesive 20 should be covered with removable release liner 22 in order to keep adhesive 20 from drying out or sticking to a surface other than the crotch portion of the panty prior to use. Any commercially available release liners commonly used for such purposes can be utilized herein. Nonlimiting examples of suitable release liners are BL 30 MG-A Silox E1/0 and BL 30 MG-A Silox 4 P/O both of which are manufactured by the Akrosil Corporation.

Central absorbent pad 12 can be essentially of any dimension. However, it is preferred that the width of central absorbent pad 12 between lines of juncture 26 and 26' be relatively quite narrow. The crotch width of panties is generally about 7.5 centimeters. If the width of central absorbent pad 12 between lines of juncture 26 and 26' is wider than the width of the panty crotch, then the walls, as discussed below, are not as apt to be formed. Without the walls, numerous benefits of the sanitary napkin of the present invention are not obtained. Furthermore, in general, the narrower the central absorbent pad 12, the longer the walls will be.

It should also be noted that a narrow central absorbent pad 12 is also effective because the overall configuration and use of the sanitary napkin 10 results in central absorbent pad 12 being maintained in close proximity to the body. Such proximity of central absorbent pad 12 places it precisely where it should be: very near the body at the vaginal opening. Central absorbent pad 12 can then absorb the vast majority of the menstrual fluid before it has an opportunity to flow along central absorbent pad 12. Thus, there is no advantage for the central absorbent pad 12 to be wide. It is preferred that the width of central absorbent pad 12 between lines of juncture 26 and 26' be from about 1 to about 11.5 centimeters, more preferably from about 2 to about 7 centimeters, and most preferably from about 2 to about 5 centimeters.

Central absorbent pad 12 need not have an absorbent capacity much larger than the total amount of menstrual fluid to be absorbed. Thus, central absorbent pad 12, in addition to being narrow, can be relatively very thin. Furthermore, a narrow and thin central absorbent pad 12 is extremely comfortable to the user.

Referring again to FIGS. 1 and 2, flap topsheet 28 is liquid permeable, permitting liquids to readily penetrate through it. Further, it is compliant and non-irritating to the wearer's skin. Flap topsheet 28 can be made of any of the conventional materials that are used for this purpose. The same materials that can be used as topsheet 14, as discussed above, can be used for flap topsheet 28. Also, as with topsheet 14, and for the same reasons, flap topsheet 28 can be treated with surfactant and can be secured such that it is in contacting relationship with flap absorbent core 30. This can be accomplished as described above.

Flap absorbent core 30 is positioned between flap topsheet 28 and flap backsheet 32. Flap absorbent core 30 provides a means for absorbing the menstrual fluid that is not absorbed by absorbent core 16. Flap absorbent core 30 is generally compressible, conformable and non-irritating to the user's skin. It can be made from any of the materials that can be used to make central absorbent core 16, as described above.

Flap backsheet 32 is impervious to liquids, thereby preventing any menstrual fluid expressed from flap absorbent core 30 from soiling the body or clothing of the user. Flap backsheet 32 can be constructed of any of the materials that can be used to construct backsheet 18, as described above.

Attached to the outer surface of flap backsheet 18 is flap adhesive 36. Flap adhesive 36 is used to assist in maintaining the flap 24 in position after it is wrapped around the edge of the crotch portion of a panty. When sanitary napkin 10 is placed in a panty for use, flap adhesive 36 is secured to the inner or outer portion of the center crotch area of the panty or to the fluid pervious top layer of the other flap. The same materials used for adhesive 20 can also be used for flap adhesive 36. Also, just as adhesive 20, flap adhesive 36 is preferably covered with removable flap release liner 38. The same release liner materials that are used for release liner 22 can also be used for flap release liner 38.

As shown in FIGS. 1 and 2, topsheet 14 and flap topsheet 28 are secured to backsheet 18 and flap backsheet 32, respectively, along seam 39. Seam 39 can be formed by any means commonly used in the art for this purpose such as by gluing, crimping or heat sealing. As an alternative to forming seam 39, topsheet 14 and flap topsheet 28 can be individually or jointly wrapped completely around the absorbent core and backsheet and be sealed to themselves by the same means used to form seal 39.

Referring again to FIGS. 1 and 2, flap 24 contains flexible axis 34. As discussed below, flap 24 is folded, in use, around the edge of the crotch portion of a panty along flexible axis 34. It is essential that flexible axis 34 be located in the body of the flap and not along the line of juncture 26. If flexible axis 34 were to be along line of juncture 26, then no wall, as discussed below, would be formed because sanitary napkin 10 would have no separate axis on which the flap 24 could be folded on itself.

It is essential that flap 24 be flexible along axis 34 so that flap 24 can fold over on itself. Such flexibility permits a good gasket-like seal to be formed between the edge of the outer fold in flap 24 and the body of the user. It also permits the portion of the flap beyond flexible axis 34 to be folded below the panty so that the outer portion of flap 24 (beyond flexible axis 34) does not chafe the leg of the user.

Numerous methods can be used to render flexible axis 34 flexible. For example, the absorbent core can be scored, compressed, reduced or eliminated along flexible axis 34. It is preferred that flexible axis 34 have a flexibility such that it has a resistance to bending through 90° of less than about 200 grams, more preferably less than about 50 grams, and most preferably less than about 25 grams as measured under TAPPI standard conditions with a PCA Score Bend Tester manufactured by the Thwing-Albert Instrument Company, Philadelphia, Pa. with a flexible axis 34 which is 7.6 centimeters long and which is maintained 2.54 centimeters above the bottom edge of the tilting plate of the tester.

Figure 3:
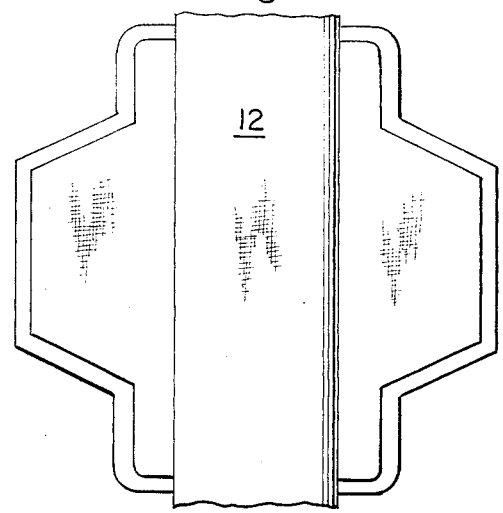
FIGS. 3, 4 and 5 are plan views of fragmentary portions of alternate sanitary napkin embodiments of the present invention.
Figure 4:
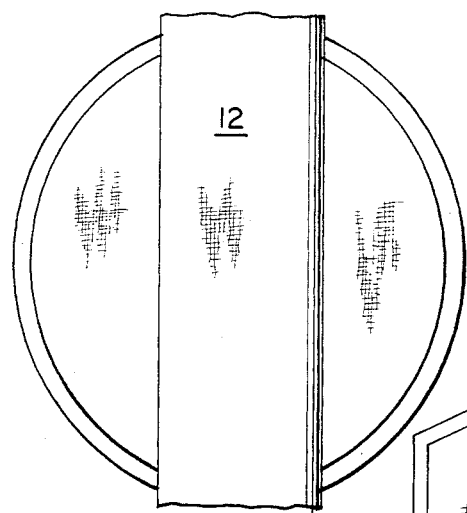
Figure 5:
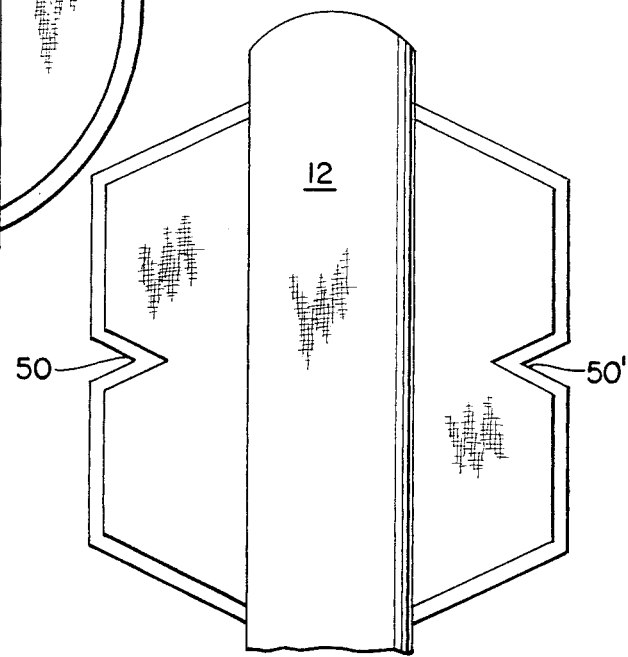

Flap 24 can be of essentially any shape; it need not be centered along the longitudinal edge of sanitary napkin 10. Exemplary shapes of flaps are shown in FIGS. 3, 4 and 5. The flaps of FIG. 3 are extended along the longitudinal edge of the central absorbent pad. Such extension provides additional protection in order to prevent soiling. The notches 50 and 50' in FIG. 5 are to permit the flap to be wrapped around the edge of the crotch portion of a panty without the flap wrinkling.

Referring to FIGS. 1 and 2, line of juncture 26 is formed where flap 24 meets the longitudinal edge of central absorbent pad 12. Flap 24 can either be integral to central absorbent pad 12 or be a separate member affixed to the central absorbent pad 12 at line of juncture 26. Topsheet 14 and flap topsheets 28 and 28' can be cut from a single continuous piece of material; backsheet 18 and flap backsheets 32 and 32' can be cut from a single piece of liquid impervious material.

It is essential that sanitary napkin 10 preferentially bend at the lines of juncture 26 and 26'. Sanitary napkin 10 preferentially bends at lines of juncture 26 and 26' because lines of juncture 26 and 26' are shorter than the longitudinal edge of central absorbent pad 12. However, if lines of juncture 26 and 26' are of the same length as central absorbent pad 12, then lines of juncture 26 and 26' must be rendered flexible so that the sanitary napkin 10 preferentially bends at lines of juncture 26 and 26'. This can be accomplished by the same methods used to render flexible axis 34 flexible.

In use, sanitary napkin 10 can be held in place by any support means well known for such purpose. Belts worn about the waist of the user can be used. The sanitary napkin can be pinned to the user's garments. Preferably, the sanitary napkin is placed in the user's panty, as described below.

Figure 6:
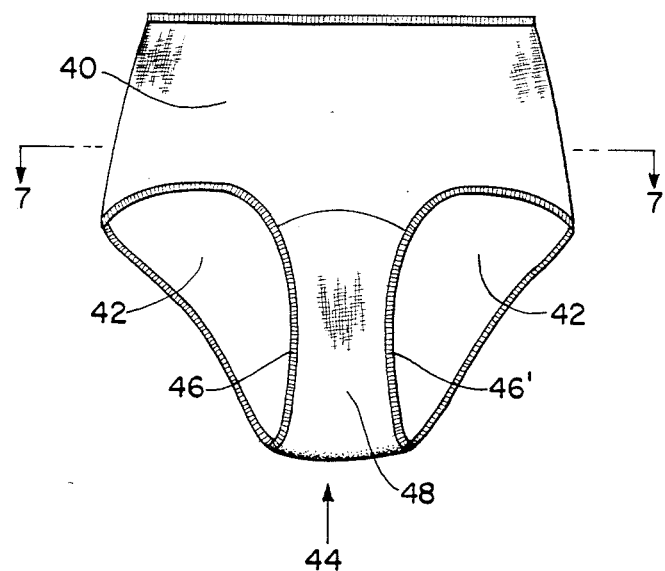
FIG. 6 is a front view of a conventional panty in which embodiments of the present invention can be used.

FIG. 6 is an undergarment of the type commonly worn by many women and well known as a panty. It comprises front section 40, back section 42, and crotch portion 44 which joins the front and back sections. The crotch portion comprises two side edges, 46 and 46', and center crotch portion 48.

Sanitary napkin 10 of the present invention is used by removing release liners 22, 38 and 38' and thereafter placing the sanitary napkin in a panty as shown in FIG.

7. The center of central absorbent pad 12 is placed in crotch portion 44 of the panty with one end of central absorbent pad 12 extending toward front section 40, and one end toward back section 42 of the panty, and with backsheet 18 in contact with the inner surface of the panty. Adhesive 20 maintains central absorbent pad 12 in such position. Flaps 24 and 24' are folded around side edges 46 and 46' of the panty along flexible axes 34 and 34'. Flap adhesives 36 and 36' secure flaps 24 and 24' in such position and thereby assist in preventing flaps 24 and 24' from becoming unwrapped from around side edges 46 and 46'. Thus flaps 24 and 24' are folded over on themselves.

Figure 7:
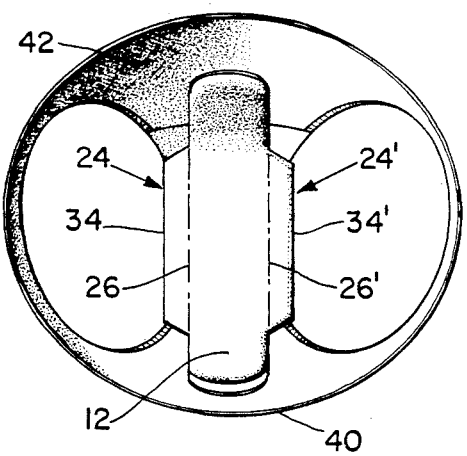
FIG. 7 is a sectional view of the panty of FIG. 6 taken along line 7—7 of FIG. 6 and having a sanitary napkin such as shown in FIG. 1 disposed therein.

Numerous benefits are derived from the use of the sanitary napkin of the present invention. Flaps 24 and 24' are wrapped around each edge of the crotch portion 44 of the panty as shown in FIG. 7. This encapsulation of the panty crotch assists in preventing the menstrual fluid from coming into contact with the center crotch portion of the panty. Thus, the center crotch portion of the panty will not be soiled.

There are two other benefits. One is that the portion of the flaps containing the flexible axes around which the flaps are folded (such as flexible axes 34 and 34' of flaps 24 and 24') provide an excellent gasket-like seal against the body. The other is that the central absorbent pad, such as central absorbent pad 12, is maintained in excellent contiguous relationship to the body.

Figure 8:
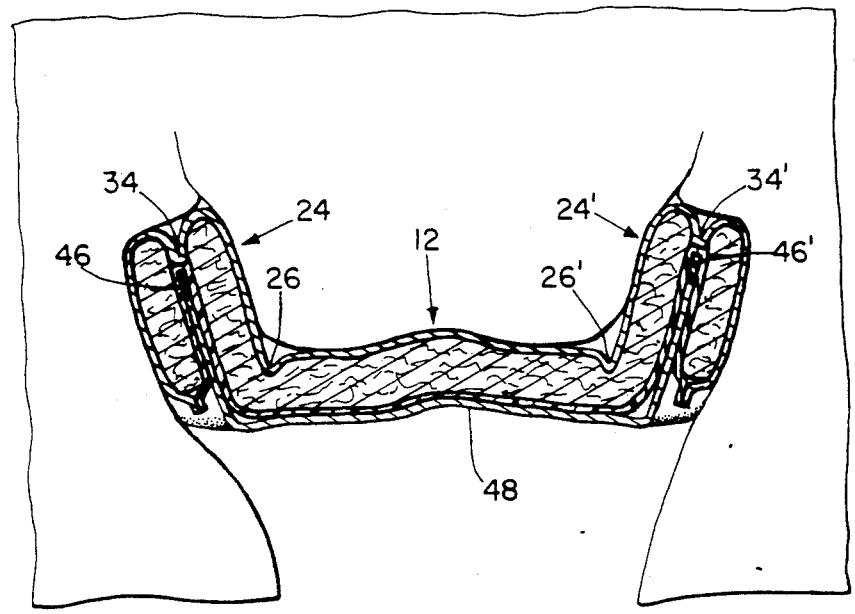
FIG. 8 is a fragmentary coronal view showing the sectioned sanitary napkin and panty of FIG. 7 in place on a user.

The edge of the crotch portion of a panty generally contains an elastic material. When a panty is worn, the elastic of the edge of the crotch portion generates an upward force, i.e., against the body, due to the energy in the elastic and the fit of the panty. The placement of the flexible axes, such as flexible axes 34 and 34', between the body and the edges of the crotch portion of the panty results in the upward force generated by the edge of the crotch portion of the panty pushing the portion of the flaps containing the flexible axes snugly against the body. This results in a gasket-like seal being formed along the flexible axes between the flaps and the body. This is illustrated in FIG. 8 which is a fragmentary coronal view showing the sectioned sanitary napkin and panty of FIG. 7 in place on a user. (A coronal view is the frontal plane that passes through the long axis of the body.) The gasket-like seal assists in preventing menstrual fluid from penetrating beyond the flexible axes which, in turn, minimizes soiling of the legs and adjoining clothing. Another benefit derived from the flaps being pushed snugly against the body along the flexible axes is that the central absorbent pad is forced into close proximity to and into conformity with the body. This, too, is illustrated in FIG. 8. The maintenance of the central absorbent pad against the body is known as "good body contact". Good body contact is beneficial because it provides a barrier to lateral flow of menstrual fluid. Without such a barrier, menstrual fluid would tend to flow quickly along the topsheet, thereby providing less time for it to be absorbed by the absorbent core. Unabsorbed menstrual fluid can flow beyond the sanitary napkin and produce clothing and body soiling.

Inherent bunching is the formation of wrinkles along the lateral axes of a sanitary napkin resulting from the initial placement of the sanitary napkin in a panty for use. This is due to the facts that a sanitary napkin is essentially linear along its longitudinal axis and that the anatomical contour of the body where the sanitary napkin is placed is essentially "U" shaped. Thus, as soon as a sanitary napkin is put in place, its shape is changed along its longitudinal axis from being essentially linear to "U" shaped. This change in shape creates wrinkles along the lateral axes of the sanitary napkin, with the vast majority of the wrinkles being at the point of greatest curvature of the body, i.e. the crotch area.

Forced bunching is the wrinkling of a sanitary napkin, along either its lateral or longitudinal axes, caused by movement of the legs of the user.

Wrinkles in a sanitary napkin created by inherent and forced bunching are known as flow channels because menstrual fluid can easily flow along the trough of the wrinkle because there is little body contact along the wrinkle.

The sanitary napkin of the present invention provides numerous benefits due to the fact that it preferentially bends at the line of juncture of each flap and the longitudinal edge of the central absorbent pad. In particular, the benefits provided are that:

(1) inherent bunching results in flow channels being formed substantially only in the central absorbent pad, not the flaps;

(2) the sanitary napkin of the present invention can withstand much forced bunching before flow channels are created;

(3) even if the forced bunching is harsh enough to create flow channels, the channels formed will be essentially limited to the central absorbent pad; and (4) even if the forced bunching is so great that flow channels are created in both the central absorbent pad and the flaps, menstrual fluid is restrained from penetrating beyond the flexible axes of the flaps.

These four benefits are obtained because the sanitary napkin of the present invention preferentially bends at the line of juncture of each flap and the longitudinal edge of the central absorbent pad. The anatomical features of the crotch area of a woman are such that the crotch width is substantially trapezoidal shaped, with the center area of the crotch, which is located at the vaginal opening, being the base of the trapezoid. When the sanitary napkin of the present invention, such as shown in FIG. 1, is in use, the anatomical features of the crotch area force the sanitary napkin to preferentially bend at the line of juncture of each flap and the longitudinal edge of the central absorbent pad. This results in the sanitary napkin forming a wall at each longitudinal edge of the central absorbent pad; the wall extends from the line of juncture of the flaps and the central absorbent pad (26, 26') to the flexible axes of the flaps (34, 34') as illustrated in FIG. 8. Thus, in use, the sanitary napkin of the present invention has a well-like shape with the plane formed by the flexible axes (34 and 34') that are wrapped around the edge of the crotch portion of the panty (46, 46') being higher than the plane formed by the lines of juncture (26 and 26').

Inherent bunching in the sanitary napkin of the present invention is substantially limited to the central absorbent pad. Essentially no flow channels are formed in the walls. Without being bound by any theory, it is believed that when the flow channels are being formed, the energy creating the flow channels is transmitted across the central absorbent pad and the flow channels are extended. This proceeds until the flow channels reach the longitudinal edges of the central absorbent pad. The flow channels extend no farther than this because, it is believed, the line of juncture of each flap and the longitudinal edge of the central absorbent pad relieves the energy extending the flow channels. Thus the flow channels will not reach the gasket-like seal and, therefore, it will remain intact. When menstrual fluid is released, the gasket-like seal will still form a dam and block the flow of the menstrual fluid. Menstrual fluid can then be absorbed by the absorbent core.

The sanitary napkin of the present invention can withstand much forced bunching before any flow channels are created because the energy transmitted to the sanitary napkin by the forced bunching results in the walls tending to rotate around each line of juncture 26 and 26'. Without such rotation flow channels would be formed. In fact, forced bunching does not result in the formation of flow channels in the sanitary napkin of the present invention until the sanitary napkin has been compressed to the width of the central absorbent pad.

Even if the forced bunching is harsh enough to create flow channels, the channels will be substantially limited to the central absorbent pad. This is true for the same reasons that inherent bunching forms flow channels only in the central absorbent pad. Therefore, the gasket-like seal will remain intact and form a dam and block the flow of menstrual fluid until it can be absorbed by the absorbent core.

Even if the forced bunching is so great that flow channels are created in both the central absorbent pad and the flaps, menstrual fluid is restrained from penetrating beyond the flexible axes of the flaps. Such flow channels are likely to break the gasket-like seal. However, menstrual fluid is restrained from penetrating beyond the flexible axes of the flaps because the walls themselves will form a barrier to flow of menstrual fluid. Menstrual fluid would have to flow up the walls, which is substantially directly against the force of gravity when the user is in an upright position, in order to penetrate the break in the gasket-like seal. Thus the walls themselves restrain the flow of the menstrual fluid.

In summary, the sanitary napkin of the present invention forms flow channels essentially only in the central absorbent pad which results in the gasket-like seal remaining intact. Thus, menstrual fluid will not flow beyond the gasket-like seal. However, if the forced bunching is so great that the gasket-like seal breaks, the walls restrain the flow of menstrual fluid.

Figure 9:
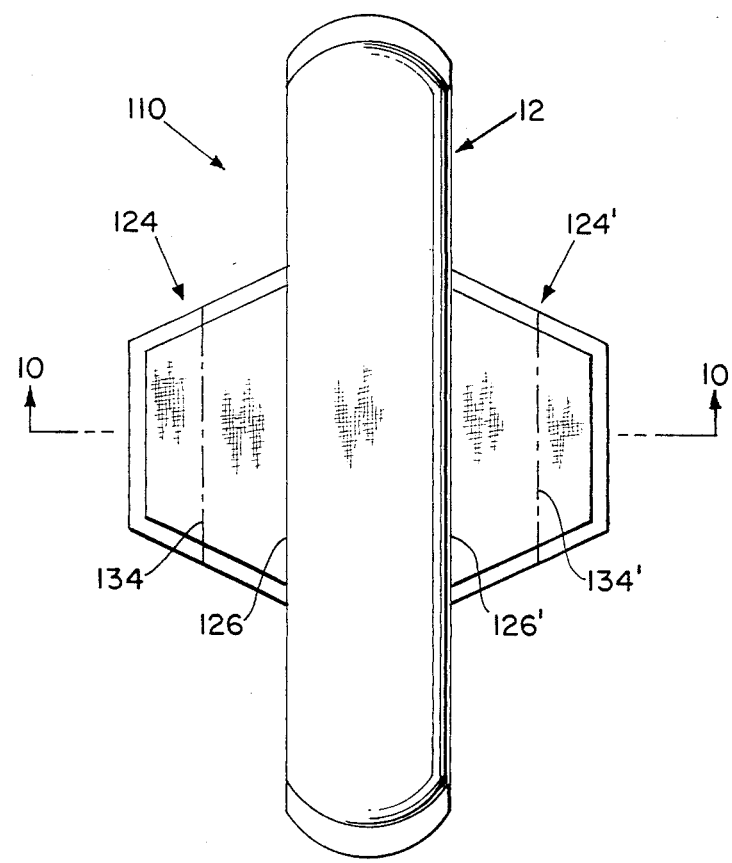
FIG. 9 is a plan view of an alternate embodiment of the sanitary napkin of the present invention.
Figure 10:
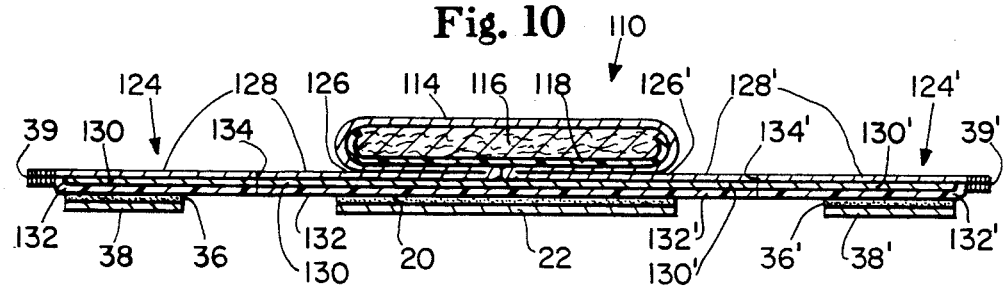
FIG. 10 is a sectional view taken along line 9—9 of FIG. 9.

FIGS. 9 and 10 illustrate an alternate embodiment of the sanitary napkin of the present invention. In these figures features and elements which are substantially identical to corresponding features and elements in FIGS. 1 and 2 are identically designated; features and elements which are functionally similar to corresponding features and elements in FIGS. 1 and 2 are identified by three digit reference numerals in which the last two digits correspond to the reference numerals used in FIGS. 1 and 2. Accordingly, the discussion of sanitary napkin 110 does not contain redundant descriptions of elements and features identical to or similar to elements and features shown in FIGS. 1 and 2. Rather, the following discussion of sanitary napkin 110 is primarily directed to the differences between it and sanitary napkin 10 of FIG. 1.

FIG. 10 shows flexible axis 134 comprising no more absorbent core than will allow it to be flexible enough to be easily wrapped around the edge of the crotch portion of a panty. Furthermore, flap absorbent core 130 of flap 124 is essentially uniform throughout flap 124. Thus any axis in the body of flap 124 can be used as flexible axis 134. It is preferred that flap 124 have a flexibility such that it has a resistance to bending through 90° of less than about 200 grams, more preferably less than about 50 grams, and most preferably less than about 25 grams as measured by the technique described above. When such a flap 124 is used, it is preferred that flap absorbent core 130 comprises layers of tissue paper.

Figure 11:
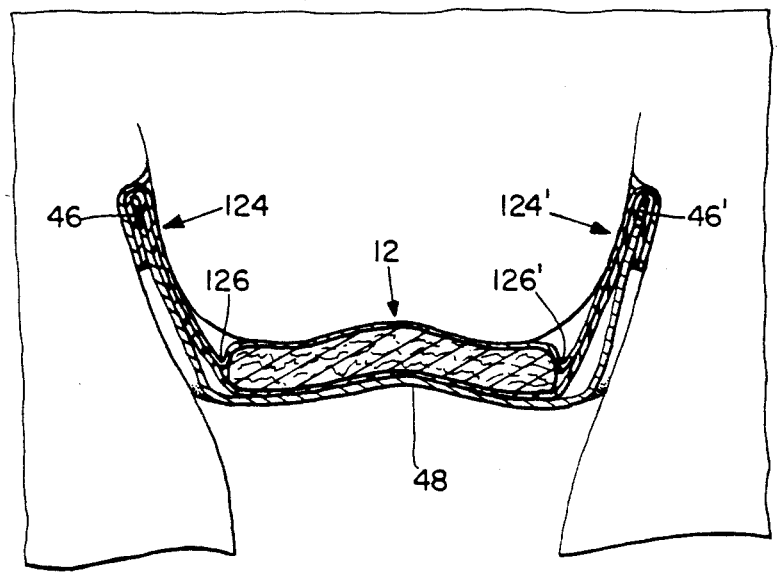
FIG. 11 is a fragmentary coronal view showing the sectioned panty of FIG. 6 and sectioned sanitary napkin of FIG. 9 in place on a user.

Such overall flexibility as that described above permits flap 124 to be wrapped around the edge of the crotch portion of a panty without the necessity of altering the natural path of the edge of the crotch portion of the panty. Thus, the edge of the crotch portion of the panty need not be stretched to fit into the flexible axis of the flap as is essential with a sanitary napkin such as sanitary napkin 10 in FIG. 1. Furthermore, the natural path of the edge of the crotch portion of a panty results, when the sanitary napkin is in place for use, in the highest wall being formed; this, in turn, provides the greatest barrier to flow of the menstrual fluid. FIG. 11 is a fragmentary coronal view showing the sectioned panty of FIG. 6 and sectioned sanitary napkin of FIG. 9 in place on a user.

Another distinction between sanitary napkin 10 of FIG. 1 and sanitary napkin 110 of FIG. 9 is that while the latter includes essentially an infinite number of flexible axes, in the former each flexible axis comprises a unique (or defined) hinge means.

It is important to note that only a minimal amount of flap absorbent core 130, or even no flap absorbent core 130 at all, is not inimical to the prevention of soiling by menstrual fluid. This is due to the fact that the primary function of the walls is menstrual fluid containment rather than absorbency. Central absorbent pad 12 absorbs the vast majority of the menstrual fluid. Furthermore, a minimal amount of flap absorbent core is much less bulky and, therefore, more comfortable to the user.

It will be understood by those skilled in the art that the invention has been described with reference to an exemplary embodiment and that variations and modifications can be effected in the described embodiments without departing from the scope and spirit of the invention.

What is claimed is:

1. A sanitary napkin that is sized and configured to be worn in a user's panties which panties are so sized and configured that the crotch edge portions can be positioned in the user's groins while the crotch region of the panties noncompressively cover the user's labia majoria, said sanitary napkin comprising a longitudinally elongate absorbent core, a liquid barrier backsheet, and a pair of flexible side flaps, said core being sized and configured to only span across the distal surfaces of the user's labia majoria, and said flaps being sufficiently flexible and sized and configured to be so disposed in a user's panties that proximal portions of said flaps extend upwardly to the user's groins and cover the laterally outwardly facing surface areas of the user's labia majoria, and so that distal portions of said flaps extend downwardly from said user's groins and are disposed intermediate edge portions of said crotch region of the user's panties and areas of the user's inner thigh regions.

2. The sanitary napkin of claim 1 wherein said medial width is about 5 centimeters.

3. The sanitary napkin of claim 1 wherein the medial width of said core is from about thirty percent to about one-hundred percent of the medial width of the crotch region of a properly sized pair of panties for said user.

4. The sanitary napkin of claim 1 wherein the medial width of said core is from about thirty to about seventy percent of the medial width of the crotch region of a properly sized pair of panties for said user.

5. The sanitary napkin of claim 1 wherein the medial width of said core is about seventy percent of the width of the crotch region of a properly sized pair of panties for said user.

6. The sanitary napkin of claim 1, 2, 3, 4, or 5 further comprising means for being releasably adhered to the crotch of the user's panties.

7. The sanitary napkin of claim 6 wherein said means for being releasably adhered to the user's panties comprises an area of adhesive on the outwardly facing surface of said sanitary napkin which area is subjacent said absorbent core whereby said sanitary napkin can be releasably adhered to the inside surface of the crotch of the user's panties.

8. The sanitary napkin of claim 6 wherein said means for being releasably adhered to the user's panties comprises a region of adhesive on the outwardly facing surface of the distal portion of each of said flaps whereby said sanitary napkin can be releasably adhered to the outer surfaces of crotch of the user's panties which regions are disposed adjacent the leg openings of the panties.

9. The sanitary napkin of claim 8 wherein said means for being releasably adhered to the user's panties further comprises an area of adhesive on the outwardly facing surface of said sanitary napkin which area is subjacent said absorbent core whereby said area can be releasably adhered to the inside surface of the crotch of the user's panties.

10. The sanitary napkin of claim 1 wherein said core has a medial width of from about 2 to about 7 centimeters.

11. The sanitary napkin of claim 10 wherein said width is from about 2 to about 5 centimeters.

12. A laterally articulated sanitary napkin comprising an elongate central absorbent core having side edges, two proximal side panels having proximal and distal edges, and two distal side panels, said proximal side panels extending laterally outward from central portions of said side edges of said central absorbent core, and having said proximal edges coextensive therewith, and said distal side panels extending laterally outward from said distal edges of said proximal side panels, said sanitary napkin further comprising means for articulating said distal side panels relative to said proximal side panels, and means for being folded along the coextensive edge portions of said central absorbent core and said proximal side panels.

13. The sanitary napkin of claim 12 wherein said central absorbent core and said proximal side panels are a unitary structure.

14. The sanitary napkin of claim 12 or 13 wherein said proximal side panels have end edges which intersect said side edges of said central absorbent core at an oblique angle.

15. The sanitary napkin of claim 12 or 13 wherein said central absorbent core is sized and configured to cover the distal portions of a user's labia majoria, said proximal side panels are sized and configured to cover laterally outwardly facing areas of the user's labia majoria and to be positioned so that said distal edges are disposed along the user's groins, and said distal side panels are configured to extend downwardly from the user's groins and be disposed adjacent the user's inner thigh areas.

* * * * *

UNITED STATES PATENT AND TRADEMARK OFFICE
CERTIFICATE OF CORRECTION

PATENT NO. : 4,589,876
DATED : May 20, 1986
INVENTOR(S) : Kees J. Van Tilburg

It is certified that error appears in the above-identified patent and that said Letters Patent is hereby corrected as shown below:

Column 10

Claim 2, line 1 "1" should be -- 10 --.

Signed and Sealed this

Fifteenth Day of August, 1995

Attest:

BRUCE LEHMAN

Attesting Officer    Commissioner of Patents and Trademarks

REEXAMINATION CERTIFICATE (1988th)
United States Patent [19]
Van Tilburg

[11] B1 4,589,876
[45] Certificate Issued  Apr. 27, 1993

[54] SANITARY NAPKIN

[75] Inventor: Kees J. Van Tilburg, Cincinnati, Ohio

[73] Assignee: The Procter & Gamble Company

Reexamination Requests:
No. 90/002,262, Jan. 28, 1991
No. 90/002,354, May 28, 1991
No. 90/002,507, Nov. 12, 1991
No. 90/002,606, Jan. 10, 1992

Reexamination Certificate for:
Patent No.: 4,589,876
Issued: May 20, 1986
Appl. No.: 591,621
Filed: Mar. 20, 1984

Related U.S. Application Data

[63] Continuation-in-part of Ser. No. 511,118, Jul. 5, 1983.

[51] Int. Cl.[5] .................. A61F 13/20; A61F 13/15
[52] U.S. Cl. .................. 604/385.1; 604/393; D24/125
[58] Field of Search .............. 604/381, 387, 375, 395, 604/370, 385.1, 385.2; 2/406

[56] References Cited

U.S. PATENT DOCUMENTS

| | | | |
|---|---|---|---|
| D. 247,372 | 2/1978 | Whitehead | D24/51 |
| 2,408,508 | 10/1946 | Canavan | 128/290 |
| 2,890,701 | 6/1959 | Weinman | 128/291 |
| 3,400,718 | 9/1968 | Saijo | 128/291 |
| 3,613,686 | 10/1971 | Waskin | 2/406 |
| 3,744,494 | 7/1973 | Marsan | 128/287 |
| 3,881,490 | 5/1975 | Whitehead et al. | 128/291 |
| 3,973,567 | 8/1976 | Srinivasan et al. | 128/290 |
| 4,285,343 | 8/1981 | McNair | 604/385.2 |
| 4,327,728 | 5/1982 | Elias | 128/285 |
| 4,327,732 | 5/1982 | Thinnes | 128/290 |
| 4,391,869 | 7/1983 | Cook et al. | 428/218 |
| 4,392,862 | 7/1983 | Marsan et al. | 604/366 |
| 4,402,689 | 9/1983 | Baum | 604/387 |
| 4,425,130 | 1/1984 | DesMarais | 604/389 |
| 4,496,359 | 1/1985 | Pigneul | 604/387 |
| 4,540,415 | 9/1985 | Kospman | 604/390 |
| 4,551,143 | 11/1985 | Cook et al. | 604/371 |

FOREIGN PATENT DOCUMENTS

| | | |
|---|---|---|
| 40-36391 | 12/1965 | Japan. |
| 46-12554 | 5/1971 | Japan. |
| 50-10718 | 4/1975 | Japan. |
| 50-100399 | 8/1975 | Japan. |
| 50-44720 | 12/1975 | Japan. |
| 52-117394 | 9/1977 | Japan. |
| 54-154696 | 4/1978 | Japan. |
| 55-16135 | 2/1980 | Japan. |
| 57-20172 | 4/1982 | Japan. |
| 2048684 | 12/1980 | United Kingdom. |

*Primary Examiner*—Randall L. Green

[57] ABSTRACT

A sanitary napkin. The sanitary napkin comprises a central absorbent pad and flaps extending from each longitudinal edge of the central absorbent pad. The body of each flap contains a flexible axis about which the flap can fold on itself. The sanitary napkin preferentially bends at the line of juncture between each flap and the longitudinal edge of the central absorbent pad. When the sanitary napkin is in a panty for use, each flap bends upwardly at the lines of juncture between the flaps and the longitudinal edges of the central absorbent pad to form the base of a wall. This wall extends to the flexible axis in the body of the flap which is folded around the edge of the crotch portion of the panty. The sanitary napkin of the present invention provides effective protection to the user during the menstrual period by preventing body and clothing soiling while being comfortable to wear.

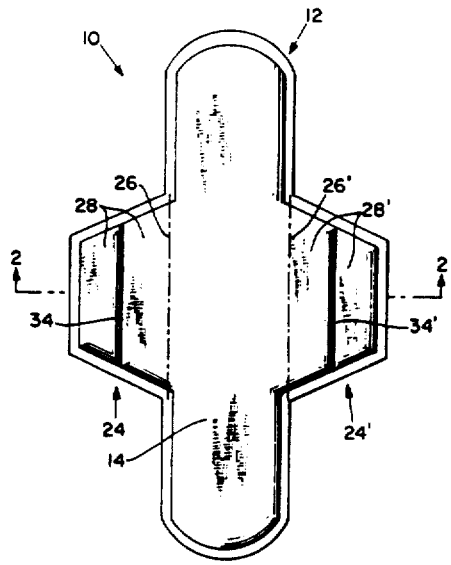

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 10, beginning after line 34 and ending before line 35.

*In summary, the present invention is directed to a sanitary napkin 10 or 110 that is sized and configured to be worn in a user's panties which are so sized and configured that the crotch edge portions 46, 46' of the panties can be positioned in the user's groins. FIGS. 8 and 11 show the relationship between the napkin, the user's panties and the user's anatomy, particularly the thighs and the labia majora which, as shown in FIGS. 8 and 11, are located between the thighs where the thighs join the trunk of the body and are covered by the crotch region 46, 48, 46' of the panties.*

*The napkin's central absorbent pad 12, which includes absorbent core 16 (or 116), extends from 26 to 26' in FIGS. 1, 2 and 8 and from 126 to 126' in FIGS. 9–11. As shown in FIGS. 8 and 11, napkin core 16 or 116 spans across and covers the distal surfaces of the user's labia majora, i.e. the surfaces located away from the connection, to the trunk of the body, of the pendulous structure shown in FIGS. 8 and 11. As also shown in FIGS. 8 and 11, the core substantially follows the contours of the labia majora so that the distal surfaces of the labia majora are substantially uncompressed and substantially undisplaced (i.e. not squashed) by the napkin core, which only spans the distal surfaces.*

*Each flap 24, 24' or 124, 124' is composed of proximal and distal portions or side panels connected at a flexible axis or hinge or articulating means 34, 34' or 134, 134' (FIGS. 1 and 9).*

*Each proximal portion or proximal side panel of each flap 24, 24' or 124, 124' extends upwardly toward one of the user's groins, which is the crease or crevice between the thigh and one of the labia majora (see FIGS. 8 and 11), and in which a crotch edge portion 46, 46' of the panties is positioned. Each of the labia majora has an outwardly facing surface area (the area facing the crease or crevice in FIGS. 8 and 11) which is covered by a proximal side panel or flap portion having a distal edge (e.g. at 34, 34' in FIG. 8) disposed along the user's groin. Each distal portion or distal side panel of a flap 24, 24' or 124, 124' extends downwardly from the user's groin and is disposed intermediate (a) an edge portion 24, 24' or 124, 124' of the crotch region of the user's panties and (b) an area of the user's inner thigh regions. In effect, each flap defines a double-walled containment dam or barrier enveloping or encapsulating a panty crotch edge portion 24, 24' or 124, 124'. In all embodiments (FIGS. 1–11) the entirety of each flap is unaffixed to the top of the central core. In the embodiment shown in FIGS. 1 and 9, not only do the proximal side panels extend outwardly from central portions of the side edges of the central core, but also the lines of juncture or coextensive edge portions of the proximal side panels and the central core are shorter than the longitudinal edges of the core.*

AS A RESULT OF REEXAMINATION, IT HAS BEEN DETERMINED THAT:

The patentability of claims 1–11 is confirmed.

Claims 12 and 13 are cancelled.

Claims 14 and 15 are determined to be patentable as amended.

New claims 16–41 are added and determined to be patentable.

14. The sanitary napkin of claim [12 or 13] *15* wherein said proximal side panels have end edges which intersect said side edges of said central absorbent core at an oblique angle.

15. The sanitary napkin of claim 12 [or 13] wherein said central absorbent core is sized and configured to cover the distal portions of a user's labia majoria, said proximal side panels are sized and configured to cover laterally outwardly facing areas of the user's labia majoria, and to be positioned so that said distal edges are disposed along the user's groins, and said distal side panels are configured to extend downwardly from the user's groins and be disposed adjacent the user's inner thigh areas.

*16. A sanitary napkin as recited in claim 1 or 10 wherein said napkin is sized and configured to be worn in a user's panties having elastic in the crotch edge portions of the panties.*

*17. A sanitary napkin as recited in claim 1 or 10 wherein said absorbent core is thicker than said side flaps.*

*18. The sanitary napkin of claim 17 wherein each of said side flaps comprises a flap topsheet and a flap backsheet.*

*19. The sanitary napkin of claim 18 wherein each of said side flaps additionally comprises a flap absorbent core positioned between said flap topsheet and said flap backsheet.*

*20. A sanitary napkin as recited in claim 1 or 10 wherein at least one of said side flaps additionally comprises a flap adhesive for securing said side flap to the outer surface of the center crotch portion of the panty or to the other of said side flaps.*

*21. The sanitary napkin of claim 20 wherein each of said side flaps comprises a flap adhesive positioned on the outer surface of said flap backsheet for securing said side flap to the outer surface of the center crotch portion of the panty or to the other of said side flaps.*

*22. A sanitary napkin as recited in claim 1 or 10 wherein each of said side flaps comprises a flexible axis and said side flap can be folded around the edge of the crotch portion of the panty at said flexible axis.*

*23. The sanitary napkin of claim 22 wherein each of said side flaps has essentially an infinite number of flexible axes so that said side flap can be folded around said edge at any of said flexible axes.*

*24. The sanitary napkin of claim 23 wherein:*
*each of said side flaps additionally comprises a flap topsheet, and flap backsheet;*
*at least one of said side flaps additionally comprises a flap adhesive for securing said side flap to the outer surface of the center crotch portion of the panty or to the other of said side flaps;* and said absorbent core is thicker than said side flaps.

25. The sanitary napkin of claim 24 wherein each of said side flaps comprises a flap adhesive positioned on the outer surface of said flap backsheet for securing said side flap to the outer surface of the center crotch portion of the panty or to the other of said side flaps.

26. The sanitary napkin of claim 22 wherein said flexible axis comprises a unique, defined hinge means.

27. A sanitary napkin as recited in claim 15 wherein said napkin is sized and configured to be worn in user's panties which is so sized and configured that the crotch edge portions of the panties can be positioned in the user's groins while the crotch region of the panties covers the user's labia majora;

each pair of proximal and distal side panels being sized and configured to encapsulate a crotch edge portion of said panties.

28. A sanitary napkin as recited in claim 27 wherein:
said distal side panels are sized and configured to be disposed intermediate (a) edge portions of the crotch region of the user's panties' and (b) the user's inner thigh regions.

29. A sanitary napkin as recited in claim 27 or 28 wherein said sanitary napkin is sized and configured to be worn in a user's panties having elastic in the crotch edge portions of the panties.

30. A sanitary napkin as recited in claim 15, 27 or 28 wherein:
each pair of said proximal and distal side panels defines a flap;
and said articulating means comprises a flexible axis on said flap.

31. A sanitary napkin as recited in claim 30 wherein:
each flap is composed of flexible material having essentially an infinite number of flexible axes so that any axis in said flap can be used as said articulating means.

32. A sanitary napkin as recited in claim 31 wherein said core is thicker than said flaps.

33. The sanitary napkin of claim 31 wherein said flap comprises a flap topsheet and a flap backsheet.

34. The sanitary napkin of claim 33 wherein said flap additionally comprises a flap absorbent core positioned between said flap topsheet and said flap backsheet.

35. The sanitary napkin of claim 34 wherein at least one of said side flaps additionally comprieses a flap adhesive for securing said side flap to the outer surface of the center crotch portion of the panty or to the other of said side flaps.

36. The sanitary napkin of claim 35 wherein each of said side flaps comprises a flap adhesive positioned on the outer surface of said flap backsheet for securing said side flap to the outer surface of the center crotch portion of the panty or to the other of said side flaps.

37. A sanitary napkin as recited in claim 30 wherein:
said flexible axis comprises a unique, defined hinge means.

38. A sanitary napkin as recited in claim 15, 27 or 28 wherein:
the entirety of each flap is unaffixed to the top of said central core.

39. The sanitary napkin of claim 12, 15, 27 or 28 wherein:
each proximal side panel and each distal side panel is sized and configured to form a double-walled barrier connected by said articulating means.

40. A sanitary napkin as recited in claim 15, 27 or 28 wherein said coextensive edge portions of said core and said proximal side panels are shorter than said side edges of said core.

41. The sanitary napkin of claim 15 wherein said central absorbent core and said proximal side panels are a unitary structure.

* * * * *